(12) United States Patent
Bhat et al.

(10) Patent No.: US 7,208,654 B2
(45) Date of Patent: Apr. 24, 2007

(54) PLANT REGULATORY SEQUENCES FOR SELECTIVE CONTROL OF GENE EXPRESSION

(75) Inventors: Deepti G. Bhat, San Diego, CA (US); Daniel J. Tennessen, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/840,987

(22) Filed: May 7, 2004

(65) Prior Publication Data

US 2005/0050582 A1 Mar. 3, 2005

Related U.S. Application Data

(60) Provisional application No. 60/468,502, filed on May 7, 2003, provisional application No. 60/482,308, filed on Jun. 25, 2003.

(51) Int. Cl.
*A01H 5/00* (2006.01)
*C12N 15/82* (2006.01)
*C07H 21/04* (2006.01)

(52) U.S. Cl. .................... 800/287; 536/24.1

(58) Field of Classification Search ................ 800/278; 435/468; 536/23.2
See application file for complete search history.

(56) References Cited

U.S. PATENT DOCUMENTS 6,084,153 A 7/2000 Good et al.
6,329,567 B1 12/2001 Jofuku et al.

OTHER PUBLICATIONS

Ulmasov et al., Composite Structure of Auxin Response Elements, The Plant Cell 7:1611-1623, 1995.*
Ito et al., Xylem-specific expression of wound-inducible rice peroxidase genes in transgenic plants, Plant Science 155:85-100, 2000.*
Lebel et al., Functional analysis of regulatory sequences controlling PR-1 gene expression in Arabidopsis, The Plant Journal 16:223-233, 1998.*
Yang et al. (2001) Expression of the REB transcriptional activator in rice grains improves the yield of recombinant proteins whose genes are controlled by a Reb-responsive promoter. PNAS, 98:11438-11443.
Wang et al. (2002) Wound-responsive regulation of the sweet potato sporamin gene promoter region. Plant Mol. Biol., 48:223-231.
De Ronde et al. (2000) Effect of antisense L-delta-pyrroline-5-carboxylate reductase transgenic soybean plants subjected to osmotic and drought stress. Plant Growth Regulation, 32:13-26.

* cited by examiner

*Primary Examiner*—Elizabeth F. McElwain
(74) *Attorney, Agent, or Firm*—Fulbright & Jaworski L.L.P.

(57) ABSTRACT

The current invention relates to enhancing gene expression in the roots, flowers, seeds, and pod wall of plants. More specifically the invention relates to a promoter that could be used to drive the expression of structural genes or other DNA sequences. We disclose the sequence of said promoter and give examples showing the function of said promoter.

4 Claims, 3 Drawing Sheets

PLANT REGULATORY SEQUENCES FOR SELECTIVE CONTROL OF GENE EXPRESSION

CROSS REFERENCE TO RELATED APPLICATIONS

This application claims benefit under 35USC § 119(e) of U.S. provisional application Ser. No. 60/468,502 filed May 7, 2003 and U.S. provisional application Ser. No. 60/482,308 filed Jun. 25, 2003, both of which are herein incorporated by reference.

FIELD OF THE INVENTION

The present invention relates to the isolation and use of nucleic acid molecules for control of gene expression in plants, specifically a novel plant promoter, and derivatives thereof. More specifically the invention relates to a promoter used to drive expression of polynucleotides preferentially, but not exclusively, in the seeds, pod wall, and flower tissues or cells of plants.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al. (1995) World Journal of Microbiology and Biotechnology 11:449–460). Particularly desirable traits or qualities of interest for plant genetic engineering would include but are not limited to resistance to insects and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous sequence that confers the desired phenotype when expressed in the plant is introduced into the plant cell. The vector also includes a plant promoter that is operably linked to the heterologous sequence, often a promoter not normally associated with the heterologous sequence. The vector is then introduced into a plant cell to produce a transformed plant cell, and the transformed plant cell is regenerated into a transgenic plant. The promoter controls expression of the introduced DNA sequence to which the promoter is operably linked.

Because the promoter plays an integral part in the overall expression of a gene or gene(s), it would be advantageous to have a variety of promoters to tailor gene expression such that a gene or gene(s) is transcribed efficiently at the right time during plant growth and development, in a desired location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, also known as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing which can be caused by interaction of homologous sequences. In light of these and other considerations, it is apparent that optimal control of gene expression and regulatory element diversity are important in plant biotechnology.

The proper regulatory sequences must be present and in the proper location with respect to the DNA sequence of interest, for the newly inserted DNA to be transcribed and translated into a protein in the plant cell. These regulatory sequences include but are not limited to a promoter, a 5' untranslated leader, and a 3' polyadenylation sequence. The ability to select the tissues in which to transcribe such foreign DNA and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include but are not limited to inducible promoters that can be triggered by external stimuli such as chemical agents, developmental stimuli, or environmental stimuli. Thus, different types of promoters may be obtained by isolating the upstream 5' regulatory regions of DNA sequences that are transcribed and expressed in a constitutive, tissue-enhanced, or inducible manner.

Particularly relevant to this invention are promoters that provide enhanced expression in the seeds, pod wall, and flowers. A selected gene expressed under the regulatory control of the disclosed promoter may change characteristics of yield, or another phenotype. The isolated promoter sequences may be used to create recombinant DNA molecules for selectively modulating expression of an operatively linked gene and provide additional regulatory element diversity in a plant expression vector in single gene or gene stacking approaches.

SUMMARY OF THE INVENTION

An isolated nucleic acid comprising SEQ ID NO:1, or its complement; or a fragment or cis element thereof, is provided herein where the isolated nucleic acid is capable of directing transcription of an operably coupled structural coding sequence. The isolated nucleic acid provided herein is a plant promoter that provides enhanced expression of an operably coupled structural coding sequence in the seed, pod wall, or flower of a plant as compared to other plant tissues. In one aspect, the plant promoter exemplified by SEQ ID NO:1 or a fragment or cis elements thereof, directs expression of an operably linked gene, structural RNAs, or polynucleotide fragments (e.g. coding sequence fragments, introns, 5' leader sequences, 3' untranslated sequences) in a sense or anti-sense direction, or in a plant expression vector for suppression of an endogenous gene, in targeted tissues or cells of a plant.

The invention also provides DNA molecule(s) that hybridize to SEQ ID NO:1 or its complement, or unique fragments or regions of SEQ ID NO:1, under stringent conditions, wherein such molecules that hybridize also confer enhanced expression in the seed, flower, or pod wall of plants of an operably linked polynucleotide.

The invention also provides recombinant DNA molecule(s) containing a nucleic acid of SEQ ID NO:1 or a functionally equivalent nucleic acid sequence identified by this application wherein the nucleic acid confers enhanced expression in the seed, flower, or pod wall of plants of a selected structural coding sequence in the DNA molecule when stably introduced into a plant cell and transmits this phenotype to a mature plant and its progeny.

The invention also provides a plant, or a propagule of said plant, containing a recombinant DNA molecule of the invention, including a transgenic plant wherein said recombinant DNA molecule confers a selected phenotype, including but not limited to disease resistance, enhanced root growth, insect resistance, herbicide tolerance, stress tolerance, increased yield, enhanced sucrose production, increased photosynthesis, ethylene responsiveness, cytokinin production or sensing, signal transduction, enhanced pod retention, decreased flower abscission, decreased pod abscission, enhanced drought tolerance, enhanced cold germination, enhanced biotic stress tolerance, increased oil, decreased sugar, and/or other biochemical pathways.

The invention also provides a DNA promoter polynucleotide isolated by a method comprising the steps of: (i) preparation of plant genomic DNA; and (ii) preparation of a DNA polynucleotide primer having substantial identity to at least ten contiguous nucleotides of SEQ ID NO: 1; and (iii) mixing the DNA polynucleotide primer and genomic DNA with a second DNA polynucleotide designed to anneal on the complementary strand; and (iv) subjecting the mixture to a DNA amplification condition that provides an amplicon; and (v) isolating the amplicon.

The invention also provides a DNA promoter polynucleotide isolated by a method comprising the steps of: (i) preparation of plant genomic DNA; and (ii) preparation of a DNA polynucleotide primer having substantial identity to at least ten nucleotides from SEQ ID NO: 1; and (iii) mixing said DNA polynucleotide primer and genomic DNA with a second DNA polynucleotide primer having substantial identity to a portion of a polynucleotide selected from an adjacent nucleic acid; and (iv) subjecting said mixture to a DNA amplification condition that provides an amplicon; and (v) isolating said amplicon.

The invention also provides for DNA construct(s) comprising a plant promoter with greater than 60% identity to SEQ ID NO:1, or an operative fragment, or cis element thereof operably linked to a heterologous polynucleotide; operably linked to a transcriptional terminator and transgenic plant(s) containing in its (their) genome as a stable insert, the DNA construct described above.

The invention also provides transgenic plants produced to contain the plant promoter described herein or functionally homologous promoter sequences that may be identified thereby and seeds from such transgenic plants, including hybrids, and progeny produced from such seeds.

DETAILED DESCRIPTION OF THE INVENTION

Plant promoters are used in agricultural biotechnology to drive the expression of heterologous genes in plants in order to obtain expression of the heterologous gene in an entire plant, or in a subset of tissues within said plant. This expression is important for the development of genetically modified horticultural and agricultural products. The present invention provides a particular plant promoter that may be used to modify or control the regulation of a desired phenotype by introducing into a plant a polynucleotide sequence of the present invention that causes the preferential expression of a heterologous gene in preferred tissues of the plant.

It is known that certain genes or structural coding sequences in a plant's native genome are expressed only at certain times in a plant's development or preferentially in certain plant tissues. Thus, one can conclude that the promoters expressing such gene functions in a manner regulating this time or tissue specific manner. Through a series of experiments referred to as transcriptional profiling, one can determine which genes are turned on in particular plant cells or tissues and/or at particular times in a plant's life cycle. Once these genes are identified, one can identify sequences unique to this gene and then through genomic analysis, probe a library of the plant's genome to ascertain the promoter region controlling that gene. By this general method, the plant promoter of the present invention was identified and isolated from a soybean genomic library. In a transcriptional profiling experiment, certain genes were identified that appeared to have preferential expression in the abscission zone of soybean. Nucleic acid primers were made and the promoter of the present invention was isolated as described in Example 1. The nucleotide sequence of this promoter is given as SEQ ID NO:1.

An important aspect of the invention provides derivatives of the disclosed promoter. In particular, the current invention includes sequences that have been derived from the promoter disclosed herein. One efficient means for preparing such derivatives comprises introducing mutations into the sequences of the invention, for example, the sequence given in SEQ ID NO:1. Such mutants may potentially have enhanced or advantageously altered function relative to the native sequence, or alternatively, may be silent with regard to function.

Mutagenesis may be carried out at random and the mutagenized sequences screened for function in a trial-by-error procedure. Alternatively, particular sequences which provide the disclosed promoter with desirable expression characteristics could be identified and these or similar sequences introduced into other related or non-related sequences via mutation. Similarly, non-essential elements may be deleted without significantly altering the function of the elements. It further is contemplated that one could mutagenize these sequences in order to enhance their utility in expressing transgenes in a particular species, for example, in maize.

The means for mutagenizing a DNA segment encoding a promoter sequence of the current invention are well-known to those of skill in the art. Mutagenesis may be performed in accordance with any of the techniques known in the art, such as, but not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 12 to about 75 nucleotides or more in length is preferred, with about 10 to about 25 or more residues on both sides of the junction of the sequence being altered. In general, the technique of site-specific mutagenesis is well known in the art, as exemplified by various publications.

The preparation of sequence variants of the selected promoter DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide-directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term "template-dependent process" refers to nucleic acid synthesis of an RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template dependent processes are available to amplify the target sequences of interest present in a sample, such methods being well known in the art and specifically disclosed herein below.

One efficient, targeted means for preparing mutagenized promoters or enhancers relies upon the identification of putative regulatory elements within the target sequence. This can be initiated by comparison with, for example, promoter sequences known to be expressed in a similar manner. Sequences which are shared among elements with similar functions or expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene that is functionally attached to each construct. As such, once a starting promoter or intron sequence is provided, any of a number of different functional deletion mutants of the starting sequence could be readily prepared.

As indicated above, deletion mutants of the promoter also could be randomly prepared and then assayed. With this strategy, a series of constructs are prepared, each containing a different portion of the clone (a subclone), and these constructs are then screened for activity. A suitable means for screening for activity is to attach a deleted promoter construct to a selectable or screenable marker, and to isolate only those cells expressing the marker protein. In this way, a number of different, deleted promoter constructs are identified which still retain the desired, or even enhanced, activity. The smallest segment that is required for activity is thereby identified through comparison of the selected constructs. This segment may then be used for the construction of vectors for the expression of exogenous protein. Thus, a functionally active region or portion of the isolated promoter, SEQ ID NO:1, is embodied within the scope of the present invention.

Therefore, in one significant aspect of the invention, nucleic acid sequences having the same or similar functionality of SEQ ID NO:1 that have 45%, 50%, 60%, 70%, 75%, 80%, 85%, 90%, or 95% identity, or is substantially identical to SEQ ID NO:1, that confers enhanced expression in the seed, flower, or pod wall of plants as compared to another part of the plant are within the scope of this invention.

As used herein, "identity" or "identical", when referring to comparisons between protein(s) or nucleic acid(s), means 98% or greater identity when nucleic acid molecules or proteins are compared over a window of more than 10 nucleotides. Thus, a first nucleic acid sequence displays "substantial identity" (or is "substantially identical") to a reference nucleic acid sequence if, when optimally aligned (with appropriate nucleotide insertions or deletions totaling less than 20 percent of the reference sequence over the window of comparison) with the other nucleic acid (or its complementary strand); there is at least about 60% nucleotide equivalence; at least about 70%; at least about 80% equivalence; at least about 85% equivalence; at least about 90%; at least about 95%; and/or at least about 98% equivalence over a comparison window of at least 20 nucleotide positions; at least 50 nucleotide positions, at least 100 nucleotide positions; over the entire length of the first nucleic acid. Optimal alignment of sequences for aligning a comparison window may be conducted by algorithms; preferably by computerized implementations of these algorithms (GAP, BESTFIT, FASTA, and TFASTA in the Wisconsin Genetics Software Package Release 7.0–10.0, Genetics Computer Group, 575 Science Dr., Madison, Wis.). The reference nucleic acid may be a full-length molecule or a portion of a longer molecule.

Nucleic acid sequences that hybridize to SEQ ID NO:1 under stringent conditions are also embodied by the present invention. Hybridization conditions are sequence dependent and will be different in different circumstances. As used herein "stringent conditions" are selected to be about 5° C. lower than the thermal melting point (Tm) for the specific sequence at a defined ionic strength and pH. The "thermal melting point" is the temperature (under defined ionic strength and pH) at which 50% of a target molecule hybridizes to a completely complementary molecule. Appropriate stringent conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6, incorporated herein by reference in its entirety. For example, the salt concentration in the wash step can be selected from a low stringent condition of about 2.0×SSC at 50° C. to a high stringency of about 0.2×SSC at 50° C. In addition, the temperature in the wash step can be increased from low stringent conditions at room temperature, about 22° C., to high stringent conditions at about 65° C. Both temperature and salt concentration may be varied, or either the temperature or the salt concentration may be held constant while the other variable is changed. For the purposes of this disclosure, stringent conditions include at least one wash in 2.0×SSC at a temperature of at least about 50° C. for 20 minutes, or equivalent conditions.

Subsets of the nucleic acid sequences of the present invention include fragments or regions of the nucleic acid molecules. "Fragment nucleic acid molecule" refers to a piece of a larger nucleic acid molecule, which may consist of significant portion(s) of, or indeed most of, the larger nucleic acid molecule, or which may comprise a smaller oligonucleotide having from about 15 to about 400 contiguous nucleotides and more preferably, about 15 to about 45 contiguous nucleotides, about 20 to about 45 contiguous nucleotides, about 15 to about 30 contiguous nucleotides, about 21 to about 30 contiguous nucleotides, about 21 to about 25 contiguous nucleotides, about 21 to about 24 contiguous nucleotides, about 19 to about 25 contiguous nucleotides, or about 21 contiguous nucleotides. Fragment nucleic acid molecules may consist of significant portion(s) of, or indeed most of, a plant coding or non-coding region, or alternatively may comprise smaller oligonucleotides. In a preferred embodiment, a fragment shows 100% identity to the plant non-coding region. In another preferred embodiment, a fragment comprises a portion of a larger nucleic acid sequence. In another aspect, a fragment nucleic acid molecule has a nucleic acid sequence that has at least 15, 25, 50, or 100 contiguous nucleotides of a nucleic acid molecule of the present invention. In a preferred embodiment, a nucleic acid molecule has a nucleic acid sequence that has at least 15, 25, 50, or 100 contiguous nucleotides of a plant non-coding region.

"Promoter" refers to a DNA sequence that binds an RNA polymerase (and often other transcription factors as well) and promotes transcription of a downstream DNA sequence. Said sequence can be an RNA that has function, such as rRNA (ribosomal RNA) or tRNA (transfer RNA). Often, the RNA produced is a hetero-nuclear (hn) RNA that has introns which are spliced out to produce an mRNA (messenger RNA). A "plant promoter" is a native or non-native promoter that is functional in plant cells.

Promoters are typically comprised of multiple distinct "cis-acting transcriptional regulatory elements," or simply "cis-elements," each of which can confer a different aspect of the overall control of gene expression. "cis elements" bind trans-acting protein factors that regulate transcription. Some cis elements bind more than one factor, and trans-acting transcription factors may interact with different affinities with more than one cis element. The promoter sequences of the present invention can contain "cis elements" which can modulate gene expression. Cis elements can be part of the promoter, or can be upstream or downstream of said promoter. Cis elements (or groups thereof) acting at a distance from a promoter are often referred to as repressors or enhancers. Enhancers act to upregulate the transcriptional initiation rate of RNA polymerase at a promoter, repressors act to decrease said rate. In some cases the same elements can be found in a promoter and an enhancer or repressor.

Cis elements can be identified by a number of techniques, including deletion analysis, i.e., deleting one or more nucleotides from the 5' end or internal to a promoter; DNA binding protein analysis using Dnase I footprinting, methylation interference, electrophoresis mobility-shift assays (EMSA or gel shift assay), in vivo genomic footprinting by ligation-mediated PCR, and other conventional assays; or by sequence similarity with known cis element motifs by conventional sequence comparison methods. Cis elements can be obtained by chemical synthesis or by cloning from promoters that includes such elements, and they can be synthesized with additional flanking sequences that contain useful restriction enzyme sites to facilitate subsequence manipulation. In one embodiment, the promoters are comprised of multiple distinct "cis-acting transcriptional regulatory elements," or simply "cis-elements," each of which can modulate a different aspect of the overall control of gene expression. For example, combinations of cis element regions or fragments of the 35S promoter can show tissue-specific patterns of expression (see U.S. Pat. No. 5,097,025). In one embodiment sequence regions comprising "cis elements" of the nucleic acid sequences of SEQ ID NO: 1 can be identified using computer programs designed specifically to identify cis elements, domains, or motifs within sequences by a comparison with known cis elements or can be used to align multiple 5' regulatory sequences to identify novel cis elements. Activity of a cloned promoter or putative promoter (cloned or produced in any number of ways including but not limited to; isolation form an endogenous piece of genomic DNA directly cloning or by PCR; chemically synthesizing the piece of DNA) can be tested in any number of ways including testing for RNA (Northern, Taqman®, quantitative PCR, etc.) or production of a protein with an activity that is testable (i.e. GUS, chlorampenicol acetyl transferase (CAT)). Multimerization of elements or partial or complete promoters can change promoter activity (i.e. e35S, U.S. Pat. Nos. 5,359,142, 5,196,525, 5,322,938, 5,164,316, and 5,424,200, and below). Cis elements may work by themselves or in concert with other elements of the same or different type, i.e. hormone- or light-responsive elements.

The technological advances of high-throughput sequencing and bioinformatics have provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced and the expressed sequences catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue-enhanced sequence can then be used as a probe or primer to clone the corresponding full-length cDNA. A genomic library of the target plant can then be used to isolate the corresponding gene and the associated regulatory elements, including promoter sequences.

The term "tissue-specific promoter" means a regulatory sequence that causes an enhancement of transcription from a downstream gene in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistols, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

The following definitions and methods are provided to better define the current invention and to guide those of ordinary skill in the art in the practice of the present invention. Unless otherwise noted, terms are to be understood according to conventional usage by those of ordinary skill in the art. Definitions of common terms used in molecular biology and molecular genetics can also be found in Lewin, *Genes VII*, Oxford University Press and Cell Press, New York, 2000; Buchanan, et al., *Biochemistry and Molecular Biology of Plants*, Courier Companies, USA, 2000; Lodish, et al., *Molecular Cell Biology*, W.H. Freeman and Co., New York, 2000. Common terms in genetics can be found in the prior as well as Lynch, et al., *Genetics and Analysis of Quantitative Traits*, Sinauer and Associates, Sunderland, Mass., 1998; Gonick, et al., *The Cartoon Guide to Genetics*, Harper Collins Publishers, New York, 1983; Hartwell, et al., *Genetics: From Genes to Genomes*, McGraw-Hill Companies, Boston, Mass., 2000; Hartl, et al., *Genetics: Analysis of Genes and Genomes*, Jones and Bartlett Publishers, Sudbury, Mass., 2000; Strachan, et al., *Human Molecular Genetics*, John Wiley and Sons, New York, 1999.

The term "amino acid sequence" means the sequence of amino acids in a polypeptide (or protein) that is written starting with the amino-terminal (N-terminal) residue and ending with the carboxyl-terminal (C-terminal) residue.

As used herein the terms "a coding sequence", "structural DNA sequence" and "a structural coding sequence" mean a nucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, and recombinant nucleotide sequences.

"Expression" means the transcription and stable accumulation of sense or antisense RNA derived from the nucleic acid molecule of the present invention. Expression may also refer to translation of mRNA into a polypeptide.

The term "a gene" means the segment of DNA that is involved in producing a polypeptide. Such segment of DNA includes regulatory sequences preceding (5' non-coding sequences) and following (3' non-coding sequences) the coding region as well as intervening sequences (introns) between individual coding segments (exons). A "Native gene" means a gene as found in nature with its own regulatory sequences. "Chimeric gene" means any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" means a native gene in its natural location in the genome of an organism. A "foreign gene" means a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

"Heterologous" sequence refers to a sequence which originates from a foreign source or species or, if from the same source or species, is modified from its original form; for example, a gene from a fungus being expressed in a plant; or a gene from the same species present under a different promoter, or a promoter driving the expression of a gene or RNA in a non-native location within the genome.

An "isolated" nucleic acid sequence or DNA molecule is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

"Native" refers to a naturally occurring ("wild-type") nucleic acid sequence.

"Nucleic acid (sequence)" or "polynucleotide (sequence)" or "DNA polynucleotide" or "DNA molecule" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

The term "nucleotide sequence" as used herein means both the sense and antisense strands of a nucleic acid molecule as either individual single strands or in the duplex. It includes, but is not limited to, self-replicating plasmids, chromosomal sequences, and infectious polymers of DNA or RNA. A nucleotide sequence is said to be the "complement" of another nucleotide sequence if they exhibit complete complementarity. As used herein, molecules are said to exhibit "complete complementarity" when every nucleotide of one of the sequences is complementary to a nucleotide of the other.

A first nucleic acid sequence is "operably linked" with a second nucleic acid sequence when the sequences are so arranged that the first nucleic acid sequence affects the function of the second nucleic-acid sequence. Often, the two sequences are part of a single contiguous nucleic acid molecule and sometimes are adjacent. For example, a promoter is operably linked to a gene if the promoter regulates or mediates transcription of the gene. A promoter is "naturally operably linked" to a structural gene if the promoter drives the transcription of the structural gene in the genome of an organism when said promoter and said structural gene are in their native locations within said genome.

"Plant cell", as used herein, includes without limitation, seeds, suspension cultures, embryos, meristematic regions, callus tissue, leaves, roots, shoots, gametophytes, sporophytes, pollen, microspores, and any other part of any of various photosynthetic, eukaryotic, multicellular or unicellular organisms of the kingdom Plantae characteristically producing embryos, containing chloroplasts, having cellulose cell walls, and often lacking the power of locomotion.

"Plant genomic DNA" is defined as DNA isolated from a plant, seed, plant tissue, tissue culture cell(s), seed(s), or any other portion of a plant wherein a portion of genetic blueprint for a plant can be isolated. Plant genomic DNA may include the contents of the nucleus of a cell, the contents of the nucleus and the organelles, or the contents of the meiotic products of a plant.

"Propagule" includes all products of meiosis and mitosis, including but not limited to, seed and parts of the plant able to propogate a new plant. For example, propagule includes a shoot, root, or other plant part that is capable of growing into an entire plant. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

Both terms "polypeptide" and "protein", as used herein, mean a polymer composed of amino acids connected by peptide bonds. An amino acid unit in a polypeptide (or protein) can be called a residue. The terms "polypeptide" and "protein" also applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a polypeptide, that polypeptide is specifically reactive to antibodies elicited to the same polypeptide but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties*, 2nd ed., T. E. Creighton, W. H. Freeman and Company, New York (1993). Many detailed reviews are available on this subject, such as, for example, those provided by Wold, F., Post-translational Protein Modifications. Perspectives and Prospects, pp. 1–12 in *Post-translational Covalent Modification of Proteins*, B. C. Johnson, Ed., Academic Press, New York (1983); Seifter et al., *Meth. Enzymol.* 182:626-M (1990) and Rattan et al., *Protein Synthesis: Post-translational Modifications and Aging, Ann. N.Y. Acad. Sci.* 663:48–62 (1992). Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine-containing and the methionine-less amino terminal variants of the polypeptide of the invention. Thus, as used herein, the terms "protein" and "polypeptide" include any protein or polypeptide that is modified by any biological or non-biological process. The terms "amino acid" and "amino acids" refer to all naturally occurring amino acids and, unless otherwise limited, known analogs of natural amino acids that can function in a similar manner as naturally occurring amino acids. This definition is meant to include, but is not limited to, norleucine, ornithine, homocysteine, and homoserine.

"Percentage of sequence identity" is determined by comparing two optimally aligned sequences over a comparison window, wherein the portion of the polynucleotide or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "recombinant DNAs" or "recombinant DNA molecules" as used herein means DNAs that contains a genetically engineered modification through manipulation via mutagenesis, restriction enzymes, and the like. The nucleic acid itself can come form either naturally occurring sources or can be created in the laboratory. It can also include all vectors created by DNA engineering, for example, all the DNA molecules included herein designated by pMON. For example, it can include molecules containing naturally occurring DNA or cDNA, or DNA molecules of synthetic origin in a plasmid, or isolated. A "recombinant" nucleic acid or "recombinant DNA molecule" can be made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., Molecular Cloning, A Laboratory Manual, Cold Spring Harbor Press, Plainview, N.Y. (1989); and Ausubel et al., *Current Protocols in Molecular Biology*, John Wiley & Sons, New York, N.Y. (1988). The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Reproductive organ" includes any numbers of organs of any type related to reproduction, including creation and propagation of meiotic products including but not limited to pollen, stamen, pistil, ovum, as well as progeny seed and plants. Reproductive organ is also inclusive of asexually produced products that can result in another plant (even a clone). Reproductive organ is specifically inclusive of flower, fruit, vegetable, grain, pod, and seed, but is not limited to these.

Polypeptides which are "substantially similar" share sequences as noted above except that residue positions which are not identical may differ by conservative amino acid changes. Conservative amino acid substitutions refer to the interchangeability of residues having similar side chains. "Conservative amino acid substitutions" mean substitutions of one or more amino acids in a native amino acid sequence with another amino acid(s) having similar side chains. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine, valine-isoleucine, phenylalanine-tyrosine, lysine-arginine, alanine-valine, aspartic acid-glutamic acid, and asparagine-glutamine. One skilled in the art will recognize that the values of the above substantial identity of nucleotide sequences can be appropriately adjusted to determine corresponding sequence identity of two nucleotide sequences encoding the polypeptides of the present invention by taking into account codon degeneracy, conservative amino acid substitutions, reading frame positioning and the like. Substantial identity of nucleotide sequences for these purposes normally means sequence identity of at least 35%.

A "substantial portion" of a nucleotide sequence comprises enough of the sequence to afford specific identification and/or isolation of a nucleic acid molecule comprising the sequence. Nucleotide sequences can be evaluated either manually by one skilled in the art, or by using computer based sequence comparison and identification tools that employ algorithms such as BLAST (Basic Local Alignment Search Tool; Altschul et al. *J. Mol. Biol.* 215:403–410 (1993)). In general, a sequence of thirty or more contiguous nucleotides is necessary in order to putatively identify a nucleotide sequence as homologous to a gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid molecule comprising the primers. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

For example, nucleic acid molecules described herein, either as cDNAs or genomic DNAs, could be isolated directly by using all or a substantial portion of the nucleic acid molecules of the present invention as DNA hybridization probes to screen cDNA or genomic libraries from any desired plant employing methodology well known to those skilled in the art. Methods for forming such libraries are well known in the art. Specific oligonucleotide probes based upon the nucleic acid molecules of the present invention can be designed and synthesized by methods known in the art. Moreover, the entire sequences of the nucleic acid molecules can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full length cDNA or genomic DNAs under conditions of appropriate stringency.

Alternatively, the nucleic acid molecules of interest can be amplified from nucleic acid samples using amplification techniques. For instance, the disclosed nucleic acid molecules may be used to define a pair of primers that can be used with the polymerase chain reaction.

In addition, two short segments of the nucleic acid molecules of the present invention may be used in polymerase chain reaction protocols to amplify longer nucleic acid molecules from DNA or cDNA produced from RNA. For example, the skilled artisan can follow the RACE protocol (Frohman et al., Proc. Natl. Acad. Sci. USA 85:8998 (1988) to generate cDNAs by using PCR to amplify copies of the region between a single point in the transcript and the 3' or 5' end. Primers oriented in the 3' and 5' directions can be designed from the nucleic acid molecules of the present invention. Using commercially available 3'RACE or 5'RACE systems (Gibco BRL, Life Technologies, Gaithersburg, Md. U.S.A.), specific 3' or 5' cDNA fragments can be isolated (Ohara et al., Proc. Natl. Acad. Sci. USA 86:5673 (1989); Loh et al., Science 243:217 (1989). Products generated by the 3' and 5' RACE procedures can be combined to generate full-length cDNAs (Frohman and Martin, Techniques 1: 165 (1989).

The term "transgenic plant" means a plant that contains an exogenous nucleic acid, which can be derived from the same plant species or from a different species. By "exogenous" it is meant that a nucleic acid molecule originates from outside the plant which the nucleic acid molecule is introduced. An exogenous nucleic acid molecule can have a naturally occurring or non-naturally occurring nucleotide sequence. One skilled in the art understands that an exogenous nucleic acid molecule can be a heterologous nucleic acid molecule derived from a different plant species than the plant into which the nucleic acid molecule is introduced or can be a nucleic acid molecule derived from the same plant species as the plant into which it is introduced. Exogenous nucleic acid molecules may be transferred into a plant cell by the use of a recombinant DNA construct (or vector) designed for such a purpose.

The promoter sequence of the present invention may be used to direct the expression in the seed, flower or pod wall of a selected plant of an operably coupled structural coding sequence where expression in those target tissues is preferred or desired to achieve the desired phenotype in the resulting transgenic plant and/or seed. One desirable phenotype is to improve the yield of a crop plant.

Many agronomic traits can affect "yield". For example, these could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, juvenile traits, efficiency of germination (including germination in stressed conditions), growth rate (including growth rate in stressed conditions), ear number, seed number per ear, seed size, composition of seed (starch, oil, protein), characteristics of seed fill. "Yield" can be measured in may ways, these might include test weight, seed weight, seed number per plant, seed weight, seed number per unit area (i.e. seeds, or weight of seeds, per acre), bushels per acre, bushels per hectare, tonnes per acre, tons per acre, kilo per hectare. In one embodiment, therefore, a transgenic plant of the present invention might exhibit an enhanced trait that is a component of yield by expressing a selected structural coding sequence under the regulatory control of the promoter of the present invention, e.g. SEQ ID NO:1 or a fragment thereof. In situations herein where a comparison is inferred between two plants, i.e. "a plant with enhanced yield", the comparison can be inferred to be between two plants wherein one contains a DNA molecule comprising a transgene, and the other is a non-transgenic plant of the same genotype, whenever possible.

The use of the promoter of the present invention may also be used to alter the composition of the plant cell, plant and/or seed of the plant species into which it is introduced, such as by altering the oil, wax, fat, protein or other compositional characteristics of the plant species and its commercially useful products.

The present invention also provides a plant recombinant DNA construct (or vector) for producing transgenic plants, wherein the plant recombinant DNA construct (or vector) comprises a nucleotide sequence described herein. Constructs or vectors may also include other genetic elements, including but not limited to, 3' transcriptional terminators, 3' polyadenylation signals, other untranslated nucleic acid sequences, transit or targeting sequences, selectable or screenable markers, promoters, enhancers, and operators. Methods which are well known to those skilled in the art may be used to prepare the plant recombinant DNA construct (or vector) of the present invention. These methods include in vitro recombinant DNA techniques, synthetic techniques, and in vivo genetic recombination. Such techniques are described in Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1988).

In addition to the promoter of the present invention operably coupled to a structural coding sequence and other regulatory elements such as a 3' polyadenylation sequence, a plant recombinant DNA construct (vector) of the present invention will typically comprise a selectable marker that confers a selectable phenotype on plant cells. Selectable markers may also be used to select for plants or plant cells that contain the exogenous nucleic acid molecules encoding polypeptides of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., *Mol. Gen. Genet.* 199:183–188 (1985)) which codes for kanamycin resistance and can be selected for using kanamycin, G418, or like selectable media; a bar gene which codes for bialaphos resistance; a mutant EPSP synthase gene (Hinchee et al., *Bio/Technology* 6:915–922 (1988)) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance and a methotrexate resistant DHFR gene (Thillet et al., *J. Biol. Chem.* 263:12500–12508 (1988)). Exemplary 3' untranslated region include, for example, a pinII 3' UTR and exemplary enhancers include the rice actin 1 intron 1, or rice actin 2 intron 1.

A plant recombinant DNA construct (vector) of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387–405 (1987)) an R-locus gene, which encodes a product that regulates the production of anthocyanin pigments (red color) in plant tissues (Dellaporta et al., Stadler Symposium 11:263–282 (1988)); a β-lactamase gene (Sutcliffe et al., *Proc. Natl. Acad. Sci. (U.S.A.)* 75:3737–3741 (1978)), a gene which encodes an enzyme for which various chromogenic substrates are known (e.g., PADAC, a chromogenic cephalosporin); a luciferase gene (Ow et al., *Science* 234:856–859 (1986)) a xylE gene (Zukowsky et al., *Proc. Natl. Acad. Sci. (U.S.A.)* 80:1101–1105 (1983)) which encodes a catechol dioxygenase that can convert chromogenic catechols; an α-amylase gene (Ikatu et al., *Bio/Technol.* 8:241–242 (1990)); a tyrosinase gene (Katz et al., *J. Gen. Microbiol.* 129:2703–2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secreted antigen that can be identified by antibody interaction, or even secreted enzymes which can be detected catalytically. Secreted proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (Biochem. Soc. Trans. 15, 17–19 (1987)) to identify transformed cells.

In preparing the recombinant DNA constructs (vectors) of the present invention, the various components of the construct or fragments thereof will normally be inserted into a convenient cloning vector, e.g., a plasmid that is capable of replication in a bacterial host, e.g., *E. coli*. Numerous cloning vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A plant recombinant DNA construct (vector) of the present invention may also include a chloroplast transit peptide, in order to target the polypeptide of the present invention to the plastid. The term "plastid" means the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region. Many plastid-localized polypeptides are expressed from nuclear genes as precursors and are targeted to the plastid by a chloroplast transit peptide (CTP), which is removed during the import steps. Examples of such chloroplast polypeptides include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. It has been demonstrated that non-plastid polypeptides may be targeted to the chloroplast by use of polypeptide fusions with a CTP and that a CTP sequence is sufficient to target a polypeptide to the plastid. Those skilled in the art will also recognize that various other recombinant DNA constructs can be made that utilize the functionality of a particular plastid transit peptide to import the enzyme into the plant cell plastid depending on the promoter tissue specificity.

Transgenic plants of the present invention preferably have incorporated into their genome or transformed into their chloroplast or plastid genomes an exogenous nucleic acid molecule (or "transgene"), that comprises at least a nucleotide sequence described herein. Transgenic plants are also meant to comprise progeny (descendant, offspring, etc.) of any generation of such a transgenic plant, and the propagules, seeds, and parts of those plants. Plant parts, without limitation, include seed, endosperm, ovule and pollen, leaves, roots, tubers, and all other products of mitosis and meiosis.

Any of the nucleic acid molecules and constructs of the invention may be introduced into a plant or plant cell in a permanent or transient manner. Preferred nucleic acid molecules and constructs of the present invention are described above and in the Examples. Another embodiment of the invention is directed to a method of producing transgenic plants which generally comprises the steps of selecting a suitable plant or plant cell, transforming the plant or plant cell with a recombinant vector, and obtaining a transformed host cell.

In a preferred embodiment the plant or cell is, or is derived from, a crop plant involved in the production of products for edible and industrial uses. Especially preferred are temperate oilseed crops and corn. Plants of interest include, but are not limited to, alfalfa, tomato, potato, rapeseed (canola and High Erucic Acid varieties), soybean, crambe, wheat, mustard, castor bean, peanut, sesame, cotton, linseed, safflower, oil palm, flax, sunflower, rye, rice, oat, barley, turfgrass, sorghum, millet, sugarcane and coconut. The invention is applicable to monocotyledonous or dicotyledonous species alike, and will be readily applicable to new and/or improved transformation and regulatory techniques.

Methods and technology for introduction of DNA into plant cells are well known to those of skill in the art, and virtually any method by which nucleic acid molecules may be introduced into a cell is suitable for use in the present invention. Non-limiting examples of suitable methods include: chemical methods; physical methods such as microinjection, electroporation, the gene gun, microprojectile bombardment, and vacuum infiltration; viral vectors; and receptor-mediated mechanisms. Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

*Agrobacterium*-mediated transfer is a widely applicable system for introducing genes into plant cells. See, e.g., Fraley et al., *Bio/Technology* 3:629–635 (1985); Rogers et al., *Methods Enzymol.* 153:253–277 (1987). The region of DNA to be transferred is defined by the border sequences and intervening DNA is usually inserted into the plant genome. Spielmann et al., *Mol. Gen. Genet.* 205:34 (1986). Modern *Agrobacterium* transformation vectors are capable of replication in *E. coli* as well as *Agrobacterium*, allowing for convenient manipulations. Klee et al., In: *Plant DNA Infectious Agents*, Hohn and Schell (eds.), Springer-Verlag, New York, pp. 179–203 (1985).

The regeneration, development and cultivation of plants from single plant protoplast transformants or from various transformed explants is well known in the art. See generally, Maliga et al., *Methods in Plant Molecular Biology*, Cold Spring Harbor Press (1995); Weissbach and Weissbach, In: *Methods for Plant Molecular Biology*, Academic Press, San Diego, Calif. (1988). Plants of the present invention can be part of or generated from a breeding program, and may also be reproduced using apomixis. Methods for the production of apomictic plants are known in the art. See, e.g., U.S. Pat. No. 5,811,636.

The transgenic plant prepared in accordance with the invention may be of any generation, including a fertile or sterile $R_0$ transgenic plant as well as seeds thereof, wherein the seed comprises SEQ ID NO:1, or a fragment, or cis element thereof. Also included within the invention are progeny plants of any generation such a fertile $R_0$ transgenic plant, wherein the progeny plant comprises SEQ ID NO:1, or a fragment, or Cis element thereof, as well as seed of a progeny plant.

Another aspect of the present invention relates to methods for obtaining a nucleic acid molecule comprising a nucleotide sequence of the present invention. One method for obtaining a nucleic acid molecule encoding all or a substantial portion of the amino acid sequence of a protein encoded on the same gene as the sequences described herein would be: (a) probing a cDNA or genomic library with a hybridization probe comprising a nucleotide sequence encoding all or a substantial portion of a DNA, cDNA, or RNA molecule described herein (b) identifying a DNA clone that hybridizes under stringent conditions to the hybridization probe; (c) isolating the DNA clone identified in step (b); and (d) sequencing the cDNA or genomic fragment that comprises the clone isolated in step (c).

Another method of the present invention for obtaining a nucleic acid molecule described herein: (a) synthesizing a first and a second oligonucleotide primer, wherein the sequences of the first and second oligonucleotide primer encode two different portions of the nucleotide sequence described herein, and are manufactured in such a way as to allow DNA amplification (for example, PCR®) (Maniatis et al., Molecular Cloning: A Laboratory Manual, Second Edition (1989) Cold Spring Harbor Laboratory, Cold Spring Harbor, N.Y.; Hartl, et al., Genetics, Analysis of genes and genomes, 5th edition, Jones and Bartlett Publishers, Inc., Sudbury, Mass.); and (b) amplifying and obtaining the nucleic acid molecule directly from genomic libraries using the first and second oligonucleotide primers of step (a) wherein the nucleic acid molecule encodes all or a substantial portion of the sequence described herein.

All or a substantial portion of the nucleic acid molecules of the present invention may also be used as probes for genetically and physically mapping the genes that they are a part of, and as markers for traits linked to those genes. Such information may be useful in plant breeding in order to develop lines with desired phenotypes. For example, the nucleic acid molecules of the present invention may be used as restriction fragment length polymorphism (RFLP) markers. Southern blots of restriction-digested plant genomic DNA may be probed with the nucleic acid fragments of the present invention. The resulting banding patterns may then be subjected to genetic analyses using computer programs such as MapMaker (Lander et al., *Genomics* 1:174–181 (1987), or can be analyzed by one skilled in the art, in order to construct a genetic map. Fragments of the present invention may be used to probe Southern blots containing restriction endonuclease-treated genomic DNAs of a set of individuals representing parent and progeny of a defined genetic cross. Segregation of the DNA polymorphisms is noted and used to calculate the position of the nucleotide sequence of the present invention in the genetic map previously obtained using this population.

Methods for determining gene expression, even expression of a gene from an introduced transgene are common in the art, and include RT-PCR, Northern blots, and Taqman®. Taqman® (PE Applied Biosystems, Foster City, Calif.) is described as a method of detecting and quantifying the presence of a DNA or RNA/cDNA molecule and is fully described in the instructions provided by the manufacturer, and at their website. Briefly, in the case of a genomic sequence a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert DNA due to successful amplification and hybridization.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989).

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application is specifically and individually indicated to be incorporated by reference.

The following examples are included to demonstrate embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings and examples is to be interpreted as illustrative and not in a limiting sense.

EXAMPLES

Example 1

Cloning the F6 Promoter (SEQ ID NO:1) into an Expression Vector

Primers dsb 135 and dsb 136 were made that are promoter specific primers with Pst1 and Nco1 overhang to help in cloning, dsb 135 (SEQ ID NO: 2) with Nco1 site at 5' end 5' GCATGCCATGGCCACAGAAAGGAACAGAAG 3' and dsb 136 (Seq ID NO: 3) with Pst1 site at 5' end 5'AAAACTGCAGAAAAGTGCAGAGAA-GAATATATACATGTCCAATCATG 3'. A PCR reaction using dsb 135 and dsb 136 was used to isolate the promoter referred to as F6 from soybean genomic DNA. The PCR reaction was set up as follows; 1 ul (less than 1 microgram but more than 50 nanograms) of soy genomic DNA, 1× Hi-Fi PCR buffer, 0.2 mm dNTP, 0.2 uM primers dsb 135 and dsb 136 and 1 ul of Taq polymerase. PCR conditions are as follows: 94° C. for 2 mins then 40 cycles at 94° C. for 15 sec, 62° C. for sec, and 68° C. for 90 sec. The PCR reaction was then held at 10 degrees Celcius until removed from machine. The PCR reaction was run on a 1% agarose gel and a ~1.1 kb band was cut out. The band was extracted using Qiagen gel extraction kit. A digest was set up in the 40 ul DNA eluted from gel with Pst1 and Nco1 using Gibco BRL's reaction 2 buffer and 10 units of each enzyme. The cloning vector used for the pF6 is pMON54989 (FIG. 1). 5 ug of pMON54989 was digested with PstI and Nco1 using the same conditions. Both DNA molecules were incubated in a 37° C. waterbath for approximately 2 hours.

Figure 1:
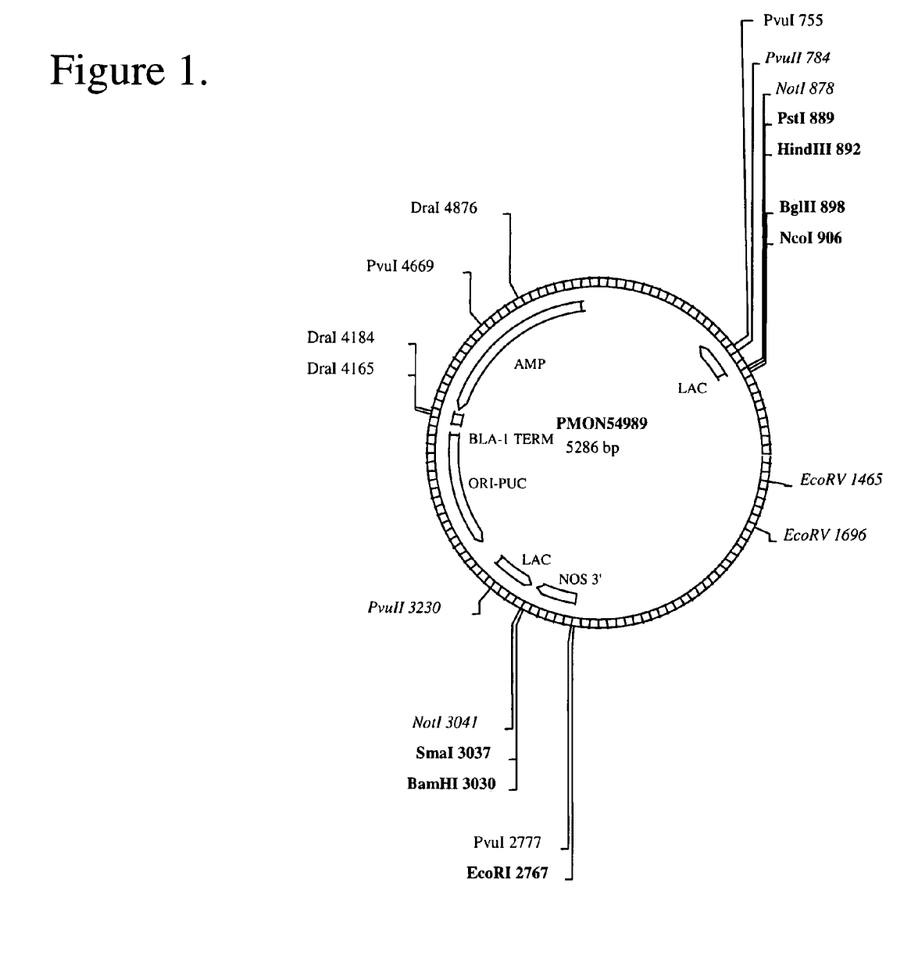
FIG. 1. This figure shows a map of pMON54989.

The digest was then run on a 1% agarose gel. The linearized pMON54989 band with Pst1 and Nco1 sites at the end and the F6 promoter band digested with Pst1 and Nco1 were cut out of the gel. The DNA was gel purified using Qiagen's gel purification kit; (QIAquick Gel extraction kit (50), cat # 28704). A ligation reaction was set up using Rapid DNA Ligation Kit (cat # 1 635379) as follows: 10 ul of digested pMON54989, 6 ul of insert; F6 promoter is added to a ligation reaction which contains 10 ul of 2× ligation buffer and 1 ul of ligase, 5 units/ul. The reaction was ligated at RT for 15 minutes. 2 ul of this ligation reaction was transformed into 100 ul of Max Efficiency DH5α Competent Cells, from Gibco-BRL, cat # 18258-012. The transformation mix was spread onto LB plates containing 100 ug/ml of ampicillin. Plates were incubated overnight at 37° C. A single colony was isolated and inoculated into 3 ml of LB containing 100 ug/ml ampicillin. Colonies were incubated at 37° C. in a shaking incubator.

Figure 2:
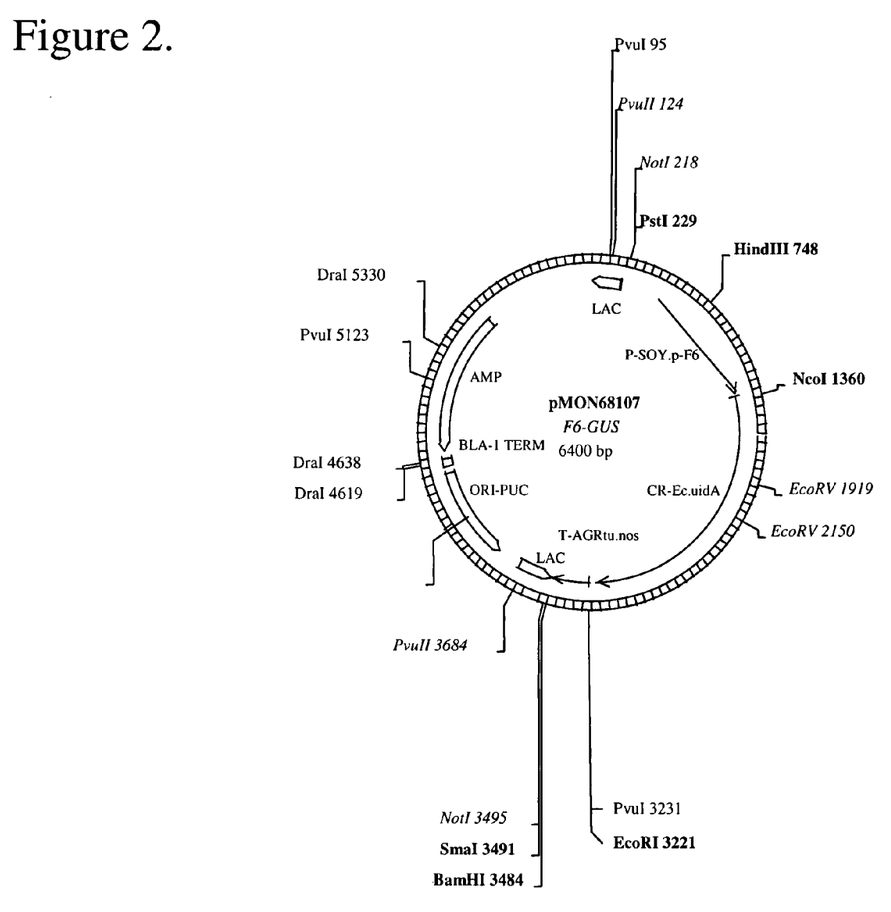
FIG. 2. This figure shows a plasmid map of DGB-HAT011942, also known as pMON68107.

A miniprep was done on the colonies using Qiagen spin miniprep kit (250), cat # 27106 (Qiagen Inc. 28159 Avenue Stanford, Valencia, Calif. 91355) according to the manufacturer's protocol. To confirm the presence of insert in the DNA, 5 ul of the minprep DNA was digested with Pst1 and Nco1. The DNA prep that showed the 1.1 kb insert was present. A large scale prep was prepared for the positive clone. This shuttle vector is called pMON68107 (FIG. 2). Presence of the correct insert was confirmed by DNA sequencing. This plasmid has pF6 driving GUS, with NOS 3' as the terminator.

Figure 3:
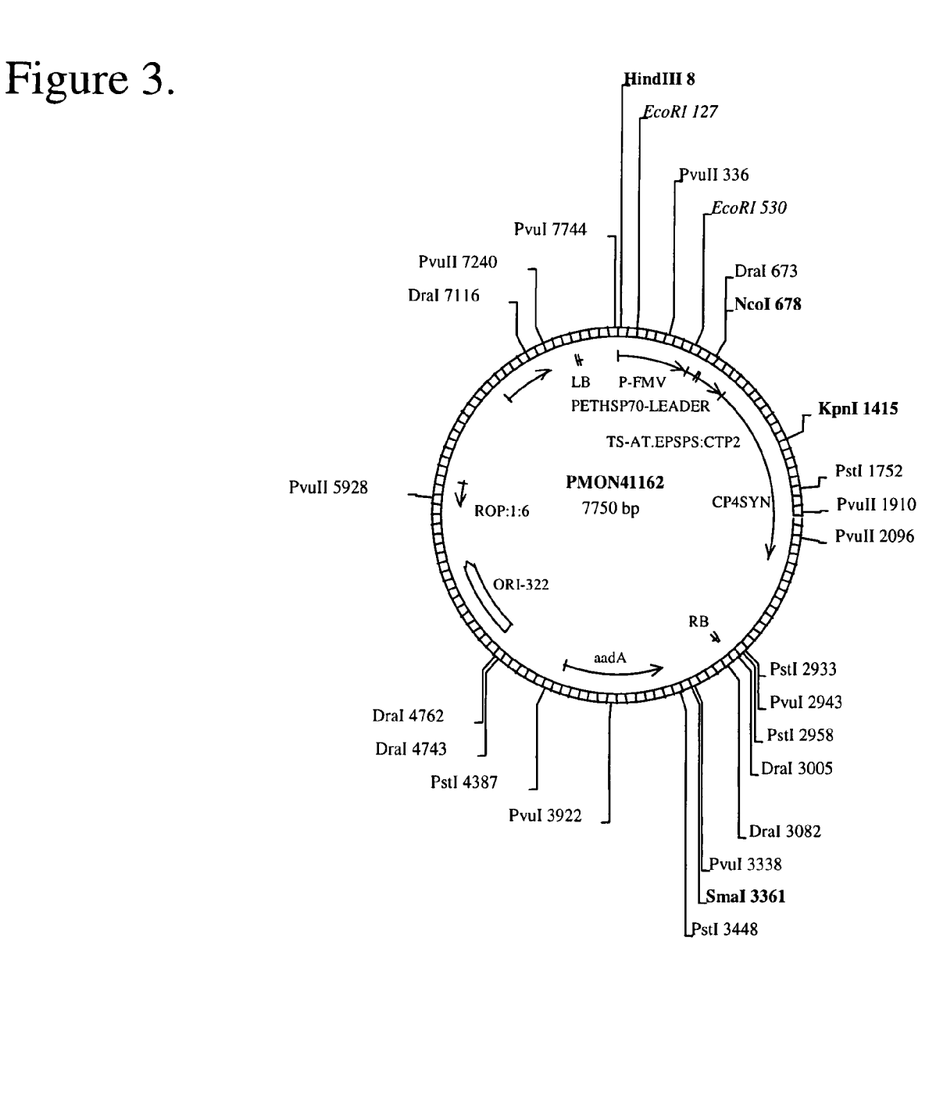
FIG. 3. This figure shows a plasmid map of pMON41162.

A large-scale prep was prepared for the above clone pMON68107, using Qiagen Plasmid Midi kit (50), cat # 12144. This was digested with Not1 to obtain the region: pF6-GUS-NOS. This insert was inserted into a 2T vector, pMON 41162 at a Not1 site (FIG. 3). pMON41162 is the binary vector used for transformation.

DNA for pMON41162 had been previously been digested with Not1 using Gibco-BRL enzyme Not1 in the presence of buffer 3. After the digestion was completed, the 5' end was de-phosphorylated to prevent self-ligation. This reaction was done in the presence of 1× phoshatase buffer and 1 unit of Calf Intestinal Alkaline Phoshatase enzyme (BMB, cat # 18009-019). Manufacturer's instruction has been followed.

DNA for pMON68107 was digested with Not1, in presence of buffer 3 (GIBCO-BRL enzyme). After the digestion was complete, both the reactions were run on an agarose gel. DNA was extracted from the gel for both pMON68107 and pMON41162. A ligation reaction was set up as follows: 2 ul of de-phosphorylated pMON41162 and 6 ul of insert of pMON68107 was added to a ligation reaction which contains 10 ul of 2× ligation buffer and 1 ul of ligase, 5 units/ul. The reaction was ligated at RT for 15 minutes. 2 ul of this ligation reaction was transformed into 100 ul of Max Efficiency DH5α Competent Cells, from Gibco-BRL, cat # 18258-012. The transformation mix was spread onto LB plates containing 50 ug/ml of streptomycin. Plates are incubated overnight at 37° C.

A miniprep was done on the colonies the next day using Qiagen spin miniprep kit (250), cat # 27106 (Qiagen Inc. 28159 Avenue Stanford, Valencia, Calif. 91355) according to the manufacturer's protocol. 5 ul of the minprep DNA was digested with Not1 to test for the appropriate insert. The digested DNA prep showed ~3 kb band, indicating it has the pF6-GUS-NOS insert in it. A largescale prep was prepared on two clones using Qiagen Plasmid Midi kit (50), cat # 12144. The final vector was pMON42503. The plasmid was checked with six different enzymes to determine the orientation of the PF6-GUS-NOS in pMON41162. The orientation where both the pF6 and P-FMV.35S.35S are located at the RB of the cassette was preferred and selected. The clone was also confirmed by DNA sequencing at the junction created by the cloning.

Example 2

Transform Soybean with the Expression Vector

Dry A3244 soybean seeds were germinated by soaking in sterile distilled water (SDW) for three minutes, drained and allowed to slowly imbibe for 2 hours at which time Bean Germination Media (BGM) was added. At approximately 12 hours, seed axis explants were isolated by removing seed coats and cotyledons. Inoculation occurred 14 hours after the addition of SDW.

Explants were placed into sterile Plantcons with 20 mL of the plasmid being transformed and resuspended to an optical density A660 of approximately 0.3 in 1/10 Gamborg's B5 media (Gamborg et al., Exp. Cell Res., 50:151–158, 1968) containing 3% glucose, 1.68 mg/L BAP, 3.9 g/L MES, 0.2M acetosyringone, 1 mM galactronic acid, and 0.25 mg/L GA3. Each Plantcon was sonicated for 20 seconds in a L&R Quantrex S140 sonicator that contained SDW +0.1% Triton X100 in the bath. Plantcons were held in place at approximately 2.5 cm below the surface of the bath liquid. Following sonication, explants were inoculated for an additional hour while shaking gently on an orbital shaker at ~90 RPM. After inoculation, the *Agrobacterium* was removed. One sheet of square filter paper and 3 mL of co-culture media containing 0–500 mM lipoic acid were added. Co-culture media consisted of 1/10 Gamborg's B5 media containing 5% glucose, 1.68 mg/L BAP, 3.9 g/L, 0.2M acetosyringone, 1 mM galactronic acid and 0.25 mg/L GA3. Explants were incubated at 23° C., dark for 3 days.

Shoots were cut 5–8 weeks post-inoculation and rooted on Bean Rooting Media (BRM) containing 25 mM glyphosate and 100 mg/L Timetin.

| BEAN GERMINATION MEDIA (BGM 2.5%) | |
|---|---|
| COMPOUND: | QUANTITY PER LITER |
| BT STOCK #1 | 10 mL |
| BT STOCK #2 | 10 mL |
| BT STOCK #3 | 3 mL |
| BT STOCK #4 | 3 mL |
| BT STOCK #5 | 1 mL |
| SUCROSE | 25 g |
| Adjust to pH 5.8. | |
| DISPENSED IN 1 LITER MEDIA BOTTLES, AUTOCLAVED | |
| ADDITIONS PRIOR TO USE: | PER 1 L |
| CEFOTAXIME (50 mg/mL) | 2.5 mL |
| FUNGICIDE STOCK | 3 mL |

BT STOCK FOR BEAN GERMINATION MEDIUM (BGM)
Make and store each stock individually. Dissolve each chemical thoroughly in the order listed before adding the next. Adjust volume of each stock accordingly. Store at 4° C.

| Bt Stock 1 (1 liter) | |
|---|---|
| KNO3 | 50.5 g |
| NH4NO3 | 24.0 g |
| MgSO4*7H2O | 49.3 g |
| KH2PO4 | 2.7 g |

-continued

| Bt Stock 2 (1 liter) | |
| --- | --- |
| CaCl2 *2H2O | 17.6 g |
| Bt Stock 3 (1 liter) | |
| H3BO3 | 0.62 g |
| MnSO4-H2O | 1.69 g |
| ZnSO4-7H2O | 0.86 g |
| KI | 0.083 g |
| NaMoO4-2H2O | 0.072 g |
| CuSO4-5H2O | 0.25 mL of 1.0 mg/mL stock |
| CoC14-6H2O | 0.25 mL of 1.0 mg/mL stock |
| Bt Stock 4 (1 liter) | |
| Na2EDTA | 1.116 g |
| FeSO47H2O | 0.834 g |
| Bt Stock 5 (500 mL) Store in a foil wrapped container | |
| Thiamine-HC1 | 0.67 g |
| Nicotinic Acid | 0.25 g |
| Pyridoxine-HC1 | 0.41 g |

| FUNGICIDE STOCK (100 mL) | |
| --- | --- |
| chlorothalonile (75% WP) | 1.0 g |
| benomyl (50% WP) | 1.0 g |
| captan (50% WP) | 1.0 g |
| Add to 100 mL of sterile distilled water. Shake well before using. Store 4° C. dark for no more than one week. | |

| BEAN ROOTING MEDIA (BRM) (for 4 L) | |
| --- | --- |
| MS Salts | 8.6 g |
| Myo-Inositol (Cell Culture Grade) | .40 g |
| Soybean Rooting Media Vitamin Stock | 8 mL |
| L-Cysteine (10 mg/mL) | 40 mL |
| Sucrose (Ultra Pure) | 120 g |
| pH 5.8 | |
| Washed Agar | 32 g |

| ADDITIONS AFTER AUTOCLAVING: | |
| --- | --- |
| BRM Hormone Stock | 20.0 mL |
| Ticarcillin/clavulanic acid (100 mg/mL Ticarcillin) | 4.0 mL |

| VITAMIN STOCK FOR SOYBEAN ROOTING MEDIA (1 liter) | |
| --- | --- |
| Glycine | 1.0 g |
| Nicotinic Acid | 0.25 g |
| Pyridoxine HC1 | 0.25 g |
| Thiamine HC1 | 0.05 g |

Dissolve one ingredient at a time, bring to volume, store in foil-covered bottle in refrigerator for no more than one month.
BRM HORMONE STOCK
Amount for 1 liter
6.0 mL IAA (0.033 mg/mL)
4.0 mL SDW
Store dark at 4° C.

Example 3

Confirmation of Transgenic Status of Plants and GUS Assays on Plant Tissues

R1 seeds from 54 events containing the construct, pMON68101. Forty seeds were planted for each event in Metro Mix soil (Scotts, Maryville, Ohio) in a greenhouse. Two leaf punches were taken for each of the samples at the first trifoliate stage. One leaf punch was used for CP4 Elisa assay, and another for a PCR reaction. The PCR assay was done with two sets of primers; one set of primers is on the 3' end of F6 promoter and the other primer on GUS towards its 5' end. This will help identify lines that are positive for the transgene and CP4. This result coupled with the CP4 Elisa assay result will be used to validate events that are free from the marker.

PCR Assay:

A single leaf punch was collected using a standard one-hole paper punch. The plant tissue was collected frozen in a 96-well format container. To extract DNA, REDExtract-N-Amp Plant PCR kit (Cat # XNA-P, Sigma, 3050 Spruce Street, St. Louis, Mo. 63103 USA) was used. DNA was extracted as follows; 100 ul of Extraction Solution was added to each well and the plate was covered with a plate sealer. The 96 well plate was heated to 95° C. for 10 minutes in a heat block. The plate was then cooled to room temperature and then again heated at 95° C. for 10 minutes. The plate was cooled to room tempersture (RT) and then spun in a microfuge before removing the plate sealer. This spinning is believed to reduce contamination of DNA across wells. To each well an equal amount of Dilution buffer is added (provided in the kit). The diluted leaf extract was then stored at 2–8° C. PCR reactions were set up for each of the plates using the above leaf extract. The following reagents were added to thin walled tubes for a polymerase chain reaction (PCR) reaction:

In a 10 ul PCR reaction; to 2 ul of the leaf disk extract was added 5 ul of REDExtract N-amp PCR reaction mix is added, (this contains buffer, salts, dNTPs, Taq polymerase and Taq Start antibody) and the two sets of primers, 0.025 um of dsb 178 (hybridizes to pF6) (SEQ ID NO: 4) 5' GTATCTGGCCATATCAACAATAGGAC 3' and 0.025 um of dsb140 hybridizes to GUS) (SEQ ID NO: 5) 5' CGT-TGCCCGCATAATTACG 3', 0.1 um of CP4 primers, Bob6 (SEQ ID NO: 6) 5' TGGTTGCTGCCTTGCTTGT 3', and Bob 7 (Seq ID NO: 7) 5' CTTGGAGCTAAGATC-GAACTCTCC 3' add 1 mm MgCl2 (this addition brought the concentration of MgCl2 to 2.5 mm total concentration and the volume up to 10 ul). PCR conditions were as follows; 94° C. for 2 mins then 94° C. for 30 sec, 52° C. for 30 sec and 68° C. for 1 min for 35 cycles. The reaction was held at 10° C. until removed. The PCR products were run on a 3% agarose SFR-Biotechnology grade gel to get a good separation between 450 bp and 500 bp PCR products. (cat # J 234, Amresco, 30175 Solon Ind. Pkwy, Solon, Ohio 44139) (Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1988).

CP4 Assay:

To a single leaf punch tissue add 300 ul of Elisa Incubation buffer (ELISA incubation buffer: 1×PBS, 0.5 ml Tween 20 per liter and 2 g BSA per liter) and three glass/steel beads, 3 mmm size. (Note: to each 100 mls of ELISA incubation buffer used for extraction with 1 tablet of Boehringer Mannheim complete protease inhibitor cocktail #1697498.) 30 ml buffer were prepared for each plate. A capmat was placed on the plate and centrifuged (at 4 degrees C.) for 5 minutes at 2000 rpm. Plates were shaken mechanically for 2 sets of three minutes and frozen until use.

Using coating buffer: Plates were coated with anti-CP4 EPSPS monoclonal antibody clone 38B6.2 lot #6199732 (3.2 mg/ml), diluted 1:3200 (3.125 ul per 10 ml). Plates were covered with plastic seal and stored in a humid box or incubated at room temperature for 4 hours or overnight at 4° C. Plates were kept for up to 2 weeks in the cold room. At the time of use plates were given 3 quick washes with (PBS-0.05% Tween 20). Diluted leaf samples (10 ul of a 300 ul leaf-punch extract plus 90 ul ELISA buffer) were loaded 100 uL/well. Plates were incubated at room temperature for 4 hours or overnight at 4° C. 3 Quick washes with (PBS-0.05% Tween) were given to each plate. 100 ul of HRP conjugate Goat anti-CP4-EPSPS (Lot 6558618) were diluted to 1:2000 in incubation buffer. Plates were incubated at RT for 2 hours at Room Temp or O/N at 4 C. Plates were then washed 3× with PBS-0.05% Tween 20. 100 uL/well of TMB substrate is added and incubated for 10 minutes at RT. TMB substrate must be at room temperature prior to use. The reaction was stopped with 50 uL 3M Phosphoric Acid (Peroxidase Reaction, not AP). The plate was read on a plate reader at 450 nm–655 nm (L1–L2) for TMB substrate.

Out of the events four events had incorporated into their genome pF6-GUS, and were free from the marker (CP4). Fourteen events had presence of marker along with pF6-GUS. These events were saved for future analysis.

Histochemical Localization of X-Glucuronidase

Using a scalpel, free-hand sections were taken for pod abscission zone and leaf abscission zone at R3 stage of soy development. The R3 stage is when flowers are blooming and a pod of about 0.5–1 cm is developing at the lowest nodes of the plant. The tissue was placed in 1×PBS with 0.1% Tween 20. The tissues were lightly fixed in 0.3% paraformaldehyde in 50 mM phosphate buffer, pH7.2 by vacuum infiltration. They were incubated in the fixative for one hour at RT. The tissues were washed in buffer 2–3×. The tissues were incubated in 0.5 mg/ml of X-Gluc for 12–24 hours at 37° C. (X-Gluconidase or 5-Bromo-4-chloro-3-indolyl-D-glucuronide cyclohexylamine salt, Rose Scientific Ltd 4027-97 Street, Edmonton, Alberta, T6E 5Y5). The tissues were rinsed 3× in potassium phosphate buffer, pH7.2. Samples were then washed in gradient EtOH (10–70% and then stored in 70% EtOH). Each of these steps can be done from 30–60 minutes each.

Stained tissues were observed under the microscope. Staining pattern is not specific to the pod abscission zones and the leaf abscission zone. Overall staining was seen to be strong all over the flower. This visual check was non-quantitative, further analysis was done to quantitate the expression.

GUS Assay

Tissues were collected from leaf, pod abscission zone, leaf abscission zone, seed, pod wall, root, and internodes at R5 stage of plant development. R5 is a stage when a pod is about 2–3 cm long, some flowers are in bud stage and others are senescing. Tissues were collected and frozen. Tissues were ground using a paint shaker with three 3 mm steel beads in a 96 well plate (~100 mg of tissue).

1 ml GUS assay buffer (0.1M KPO4, pH7.8, 10 mM DTT, 1 mM EDTA) was added to the ground tissue sample. The sample was spun for 10' in a cold room.

For Protein Assay

Prepare fresh BSA standards range between 0.5 ug to 20 ug.

For each 2–10 ul of sample add 50 ul of Bradford dye and bring the volume up to 200 ul. The protein quantity is read at 590 nm. Make sure all the samples range fall in between the standards range—if not, dilute appropriately based on the reading.

For GUS Assay

In a 96 well plate take 240 ul of 2.5 mM MUG buffer (4-Methylumbelliferyl α-D-Glucuronidase, MUG, # M-9130, Sigma) and to it add 10 ul of the extracted sample. The samples were then read under endpoint wavelength 355 nm and then read under a kinetic setting at 460 nm. The slope value from the standard reading that is obtained from endpoint reading is used for calculating GUS value. The data from the plate in Kinetic was studied using an excel sheet which has the calculated pmol/MU/min (turnover rate of GUS enzyme). A standard GUS control is prepared in the range of 50–1600 pmol/MU using 4-Methylumbelliferone or 7-hydroxyl-4-methyl coumarin (# M-1508, Sigma).

GUS values were obtained from each tissue, results are shown in Table 1. Based on the data shown in Table 1 it can be seen that the F6 promoter causes increased expression in the seed, pod wall, and flower. On a less consistent basis the expression is also increased in abscission zone(s), root, and leaf. Variation in transgenic experiments of this type is normal and can be due to insertion site effects, random variation, chromatin structure, a mix of these, and/or other reasons.

TABLE 1

The GUS expression is seen to be highest in seed, pod wall, root, and flower.

| | leaf | internode | Pedicel AZ | Leaf AZ | Seed | Pod wall | Root | Flower |
|---|---|---|---|---|---|---|---|---|
| 22401 (n = 6) | 936 | 1629 | 27925 | 72798 | 137782 | 82495 | 1100 | 51172 |
| 22401 (n = 7) | 1069533 | 449651 | 450703 | 400048 | 1526944 | 1159560 | 184274 | 3096655 |
| 22457 | 75766 | 145932 | 195759 | 18948 | 132119 | 381909 | 26370 | 174464 |
| A3244 (n = 2) | 0 | 0 | 0 | 0 | 0 | 0 | 0 | 0 |
| FMV (n = 2) | 0 | 284237 | 303519 | 348381 | 6859714 | 3156980 | 89045 | 3135847 |

What is claimed is:

1. An isolated DNA molecule that has promoter activity in a plant cell and that has a sequence comprising SEQ ID NO:1 or its complement, or that comprises a fragment comprising contiguous nucleotides of SEQ ID NO: 1 or its complement wherein the fragment retains the promoter activity of SEQ ID NO: 1.

2. The isolated DNA molecule of claim 1, wherein said promoter activity is enhanced in a tissue selected from the group consisting of seed, pod wall, flower, pod abscission zone, leaf abscission zone, root, and leaf.

3. A recombinant DNA molecule comprising the isolated DNA molecule of claim 1 operably linked to a polynucleotide.

4. A stably transformed crop plant having in its genome the recombinant DNA molecule of claim 3.

* * * * *

SEQUENCE LISTING

<160> NUMBER OF SEQ ID NOS: 7

<210> SEQ ID NO 1
<211> LENGTH: 1131
<212> TYPE: DNA
<213> ORGANISM: Glycine max

<400> SEQUENCE: 1

| gaaaagtgca gagaagaata tatacatgtc caatcatgaa ctagaaccag atactttgt | 60 |
| aatacataca caccaccatc ttcggtgtct gatgtttctg ctagcaaatc tgaagaatag | 120 |
| acataataac ttccttgttt aaccaccaat gcagtatcaa agatataaaa tcgaacctcg | 180 |
| catccttgta ctgtagattg attattcaga atgagaata ctgttggcta atgctttagc | 240 |
| ttattctttg cattgtattt gtctttcact caaattatgc aaagttacaa agtccctca | 300 |
| catagttgtg agtgtcagtt atgatactgt accaatgaaa ttattctatt gaaccagcta | 360 |
| aggtgtttat tctaatctag gaggacaata gtaccgtgta caagatgttt tcacacgcca | 420 |
| atggaaacga gtgatgtagg ggagcatctt aatcataaaa ccataaaatt tttcagatca | 480 |
| tgtgctctgt ctaattctca ttgttactta gcacagctaa gcttttggaa gttttgttat | 540 |
| ccattatgca accttttgca tgattgtttc catagaatgt accctataaa attttgttt | 600 |
| tcgtagaacc tcaattctga aatcattaag ctgaaatcaa gtaaatgttt tatggggcc | 660 |
| acacaatgaa tggcatcagc attaattgtt tgtttccaat tgggttgcac tgatttagtg | 720 |
| acaacaagag aggatagata aattaaacaa aaaagagaga aagatttttt ttaagaagag | 780 |
| ttgtatctgg ccatatcaac aataggacaa aacttgcaaa aaaagatttt aaggtattta | 840 |
| tggcattatc taaaaaaaag tacttaaggt attatactcc aataaaaaat aataatacgt | 900 |
| gtattatttt atttacctca atttaggacc attaaaatga aggacattga ctaaaaaat | 960 |
| aatacacatg tttttattga aaaataacat tacaagcatc aaacaaactt tatgctataa | 1020 |
| tatacacata cctatctata aataaacaca ctaaatgcat ttcacaccaa gtgaacatta | 1080 |
| agtgttatac actactcttg cgtgagttct tcttctgttc ctttctgtgg c | 1131 |

<210> SEQ ID NO 2
<211> LENGTH: 30
<212> TYPE: DNA
<213> ORGANISM: Artificial
<220> FEATURE:
<223> OTHER INFORMATION: Glycine max with additional 5' NcoI site

<400> SEQUENCE: 2

| gcatgccatg gccacagaaa ggaacagaag | 30 |

<210> SEQ ID NO 3
<211> LENGTH: 47
<212> TYPE: DNA
<213> ORGANISM: Artificial
<220> FEATURE:
<223> OTHER INFORMATION: Glycine max with additional 5' PstI

<400> SEQUENCE: 3

| aaaactgcag aaaagtgcag agaagaatat atacatgtcc aatcatg | 47 |

<210> SEQ ID NO 4
<211> LENGTH: 26
<212> TYPE: DNA
<213> ORGANISM: Glycine max

```
<400> SEQUENCE: 4
gtatctggcc atatcaacaa taggac                                          26

<210> SEQ ID NO 5
<211> LENGTH: 19
<212> TYPE: DNA
<213> ORGANISM: Artificial
<220> FEATURE:
<223> OTHER INFORMATION: Hybridizes to GUS reporter gene

<400> SEQUENCE: 5
cgttgcccgc ataattacg                                                  19

<210> SEQ ID NO 6
<211> LENGTH: 19
<212> TYPE: DNA
<213> ORGANISM: Artificial
<220> FEATURE:
<223> OTHER INFORMATION: Hybridizes to CP4 EPSPS

<400> SEQUENCE: 6
tggttgctgc cttgcttgt                                                  19

<210> SEQ ID NO 7
<211> LENGTH: 24
<212> TYPE: DNA
<213> ORGANISM: Artificial
<220> FEATURE:
<223> OTHER INFORMATION: Hybridizes to CP4 EPSPS

<400> SEQUENCE: 7
cttggagcta agatcgaact ctcc                                            24
```